(12) United States Patent
Kwak (10) Patent No.: US 12,427,103 B2
(45) Date of Patent: Sep. 30, 2025

(54) **COSMETIC COMPOSITION CONTAINING *HIBISCUS MANIHOT* L. EXTRACT AND METHOD FOR PREPARING THE SAME**

(71) Applicant: ALL IN ON Co., Ltd, Seoul (KR)

(72) Inventor: Jong Bock Kwak, Seoul (KR)

(73) Assignee: ALL IN ON Co., Ltd, Seoul (KR)

( * ) Notice: Subject to any disclaimer, the term of this patent is extended or adjusted under 35 U.S.C. 154(b) by 387 days.

(21) Appl. No.: 17/974,427

(22) Filed: Oct. 26, 2022

(65) Prior Publication Data

US 2024/0065965 A1    Feb. 29, 2024

(30) Foreign Application Priority Data

Aug. 24, 2022    (KR) .................. 10-2022-0106071

(51) Int. Cl.
*A61K 36/00*    (2006.01)
*A61K 8/9789*    (2017.01)
*A61Q 17/00*    (2006.01)
*A61Q 19/08*    (2006.01)

(52) U.S. Cl.
CPC ............ *A61K 8/9789* (2017.08); *A61Q 17/00* (2013.01); *A61Q 19/08* (2013.01)

(58) Field of Classification Search
CPC ...................................... A61Q 19/00
See application file for complete search history.

(56) References Cited

FOREIGN PATENT DOCUMENTS

CN    107362108 A  * 11/2017
KR    10-2022-0068779 A    5/2022

* cited by examiner

*Primary Examiner* — Qiuwen Mi
(74) *Attorney, Agent, or Firm* — Heedong Chae; Lucem, PC (57) ABSTRACT

One aspect of the present disclosure relates to a cosmetic composition comprising *Hibiscus Manihot* L. extract and a method for preparing the same, which has an effect of improving skin elasticity, alleviating skin wrinkles, etc.

2 Claims, 8 Drawing Sheets

COSMETIC COMPOSITION CONTAINING *HIBISCUS MANIHOT* L. EXTRACT AND METHOD FOR PREPARING THE SAME

CROSS REFERENCE TO RELATED APPLICATION

The present application claims priority to Korean Patent Application No. 10-2022-0106071, filed on Aug. 24, 2022, the entire contents of which is incorporated herein for all purposes by this reference.

BACKGROUND OF THE INVENTION

1. Field of the Invention

One aspect of the present disclosure relates to a cosmetic composition, and more specifically, to a cosmetic composition containing an extract of *Hibiscus Manihot* L. and a method for preparing the same, which contains the extract of *Hibiscus Manihot* L., so as to have an effect of improving skin elasticity, alleviating skin wrinkles, etc.

2. Description of the Prior Art

The skin is a part of the body which is directly exposed to an external environment, and the skin not only acts as a protective film to protect important organs of our body, but also serves to control water evaporation and protect the body from external infections. However, no matter how much the skin blocks the penetration of viruses from the outside, external stress such as excessive ultraviolet rays, fine dust, polluted environments, and the like, causes skin irritation, which ultimately leads to skin aging.

Collagen is one of the most abundant fibrous proteins in the body of animals. Collagen is a main component of the dermal layer and connective tissue of the skin, and accounts for 90% of the proteins which make up bones. Collagen, which is generally used for medical or cosmetic purposes, is extracted from animal bones and skin, and is a high molecular weight protein composed of three polypeptide chains with a molecular weight of about 100,000 to form a helical structure.

With the molecular weight of approximate 130,000, collagen is a polypeptide which constitutes one third of mammalian tissues (a main component of skin, connective tissues, and organic materials of bones and teeth). Collagen is prepared by dissolving mineral parts of bone with phosphoric acid. The separation from the tissues is sequentially performed by an organic solvent extraction, acid-alkali treatment, and then an action of trypsin hyaluronidase, so as to obtain collagen as an insoluble material. The constituent amino acids include proline, oxyproline (hydroxyproline), glycine, glutamic acid, and the like, out of which collagen is characterized by having a high content of oxyproline, which is not present in other proteins.

Most of the collagen currently in circulation is animal collagen prepared by selecting raw materials from cattle, thus raising concerns over foot-and-mouth disease, mad cow disease, and the like. Accordingly, there is an emerging need for development of plant proteins (hereinafter referred to as "plant collagen") containing hydroxy proline, hydroxy lysine, etc., which are the main components of collagen, in order to compensate for the vulnerability of animal collagen prepared by selecting raw materials from cattle, which has been used with anxiety.

Meanwhile, reactive oxygen species are highly reactive oxygen radicals generated by oxygen molecules due to a special arrangement of electrons in an electron shell when an organism generates energy through respiration. The reactive oxygen species generated as above are a kind of free radical, and the reactive oxygen species are highly reactive and thus cause oxidative damage to tissues by destroying lipids, proteins, and DNA, which are the main components of cells. Chronic oxidative damage is a cause of various chronic diseases, such as aging or cancer, as well as deterioration of cell functions.

The reactive oxygen species (ROS) includes peroxide anions, hydrogen peroxide ($H_2O_2$) and hydroxyl radicals (OH), which are mainly produced in the cytosol or granules like the mitochondria or microsome in cells.

The reactive oxygen species is constantly generated not only in a normal energy metabolism process but also by various mechanisms, while the reactive oxygen species is also removed by various enzymes and non-enzymatic antioxidants, so that the generation and elimination thereof keep a balance therebetween in a normal living body. Examples of enzymatic antioxidants present in the living body include superoxide dismutase (SOD), catalase, etc., and non-enzymatic antioxidants are known to include vitamin C, tocopherol, reduced glutathione, selenium, uric acid, etc. The activity of the antioxidants in the human body protects the reactive oxygen species from doing damage to lipids, proteins and nucleic acids in cells.

In addition, an appropriate amount of reactive oxygen species acts as an intracellular signal transduction material, and thus plays an important role in maintaining cellular functions such as an activation of an electron transport system in mitochondria and leukocyte cells. However, the excessively generated reactive oxygen species causes oxidative stress by disrupting an antioxidant balance in the living body.

The oxidative stress is a factor which gives stress to cells, reacts with various substances in the body, attacks cells, induces irreversible damage to cells and tissues, or causes mutations, cytotoxicity, carcinogenesis and the like, and thus is known as a key etiological cause of various diseases such as brain disease, heart disease, arteriosclerosis, diabetes, pulmonary fibrosis, cancer, arthritis, dementia, and the like, as well as aging.

Meanwhile, ultraviolet rays are divided into ultraviolet C (UVC, 200 to 280 nm), ultraviolet B (UVB, 280 to 320 nm), and ultraviolet A (UVA, 320 to 400 nm) according to the wavelength, and the ultraviolet C has a short wavelength, most of which is absorbed by the earth's ozone layer and does not reach the earth's surface.

Ultraviolet B (UVB radiation, wavelength: 280-320 nm) is one of the major environmental factors which cause harmful effects on the skin, such as skin cancer, suppression of the immune system, photo-aging, and the like. The reactive oxygen species (ROS) generated by the ultraviolet B causes oxidative damage to cellular components such as lipids, proteins, and DNA, and consequently promotes skin aging and cause various skin lesions.

Meanwhile, fine dust is an air pollutant containing harmful substances such as sulfurous acid gas, nitrogen oxides, heavy metals, ozone, carbon monoxide, and the like, and is generated from automobiles, factories, and the like, and refers to substances floating in the air for a long time. When the particle diameter of the fine dust is 10 μm or less, it is denoted as PM 10, and when the particle diameter of the fine dust is 2.5 μm or less, it is denoted as PM 2.5, which is called "ultra-fine dust" or "fine particulate matter."

The fine dust enters the body not only through the nose and mouth, but also through the skin. The skin of the human body is largely composed of an epidermal layer and a dermal layer, and the epidermal layer forms a protective film (skin barrier) like a dense stack of bricks to prevent penetration of dust and the like into the body. However, the fine dust containing heavy metals, environmental hormones and the like may break down the skin barrier and penetrate into the body.

The fine dust containing the above toxic chemicals causes cell transformation in contact with the skin, which causes cracks in the skin barrier, so that various carcinogens, environmental hormones and the like contained in the fine dust can easily penetrate into the human body. The size of the pores of the human body is two to five times the size of fine dust (about 0.01 mm), which can thus easily pass through the pores.

Accordingly, the fine dust acts as a major cause of various skin diseases. The danger of ultra-fine dust, which contains heavy metals, such as lead, cadmium, etc., and various chemicals, weakens a metabolic flow of the skin, thus lowering a function of controlling sebum, and causing dryness, itchiness, and skin troubles. Harmful substances such as heavy metals, environmental hormones and the like contained in the fine dust promote the secretion of inflammatory cytokines in cells and increase the number of leukocytes, which also causes allergic reactions in atopic dermatitis.

In order to protect the skin from the threat of the external environment, cases of using natural plants are increasing. As a related technology, Korean Unexamined Patent Publication No. 10-2022-0068779 (publicized on May 26, 2022) discloses "Method for preparing a fermented extract of *Hibiscus Manihot* L., and a cosmetic composition for skin moisturization and elasticity enhancement," and relates to a method for preparing a fermented extract of *Hibiscus Manihot* L., which includes: a first step of preparing *Hibiscus Manihot* L. powder; a second step of preparing a solution containing the *Hibiscus Manihot* L. powder and water; a third step of preparing a strain culture solution by inoculating the solution with the strain culture solution; a fourth step of preparing a fermented broth by fermenting the strain culture solution; a fifth step of aging the fermented broth; a sixth step of heat-treating the fermented broth subjected to the fifth step; a seventh step of centrifuging the fermented broth subjected to the sixth step to obtain a supernatant; and an eighth step of preparing a fermented extract by adding an additive to the filtrate obtained by stirring and filtering the supernatant.

However, the conventional fermented extract of *Hibiscus Manihot* L. has a problem in that it cannot maximize the active material of *Hibiscus Manihot* L. (Gold *Hibiscus*), and thus there is a growing need for an extraction method capable of maximizing the effective active material in Gold *Hibiscus* and an extract of Gold *Hibiscus* prepared therethrough.

RELATED ART REFERENCES

Patent Documents (Patent Document 0001) Korean Unexamined Patent Publication No. 10-2022-0068779 (publicized on May 26, 2022), "Method for preparing a fermented extract of *Hibiscus Manihot* L., and a cosmetic composition for skin moisturization and elasticity enhancement"

SUMMARY OF THE INVENTION

In order to solve the above problems, one aspect of the present disclosure may provide a cosmetic composition containing an extract of *Hibiscus manihot* L. and a method for preparing the same, which contains the extract of *Hibiscus manihot* L., thus having an effect of improving skin elasticity, alleviating skin wrinkles, etc.

In order to achieve the above objects, one aspect of the present disclosure may provide a cosmetic composition containing an extract of *Hibiscus manihot* L., which is obtained by performing a supercritical extraction on *Hibiscus manihot* L.

In addition, the extract of *Hibiscus manihot* L. may be obtained by performing the supercritical extraction on a flower portion of *Hibiscus manihot* L.

Furthermore, the extract of *Hibiscus manihot* L. may be obtained by performing the supercritical extraction on *Hibiscus manihot* L. through supercritical fluid containing carbon dioxide at a temperature of 40 to 120° C. and atmospheric pressure of 90 to 650.

Moreover, one aspect of the present disclosure may provide a method for preparing a cosmetic composition containing an extract of *Hibiscus manihot* L., which includes: a pulverizing step (S10) of pulverizing *Hibiscus manihot* L., to prepare pulverized *Hibiscus manihot* L.; and a supercritical extraction step (S20) of obtaining an extract of *Hibiscus manihot* L. by performing a supercritical extraction on *Hibiscus manihot* L. through supercritical fluid containing carbon dioxide.

Besides, in the supercritical extraction step (S20), the supercritical extraction may be performed on the pulverized *Hibiscus manihot* L. through supercritical fluid containing carbon dioxide at a temperature of 40 to 120° C. and pressure of 90 to 650.

A cosmetic composition containing an extract of *Hibiscus manihot* L. according to a preparation method of the present disclosure can have an effect of improving skin elasticity, an effect of alleviating skin wrinkles, etc.

DETAILED DESCRIPTION OF THE EXEMPLARY EMBODIMENTS

Figure 1:
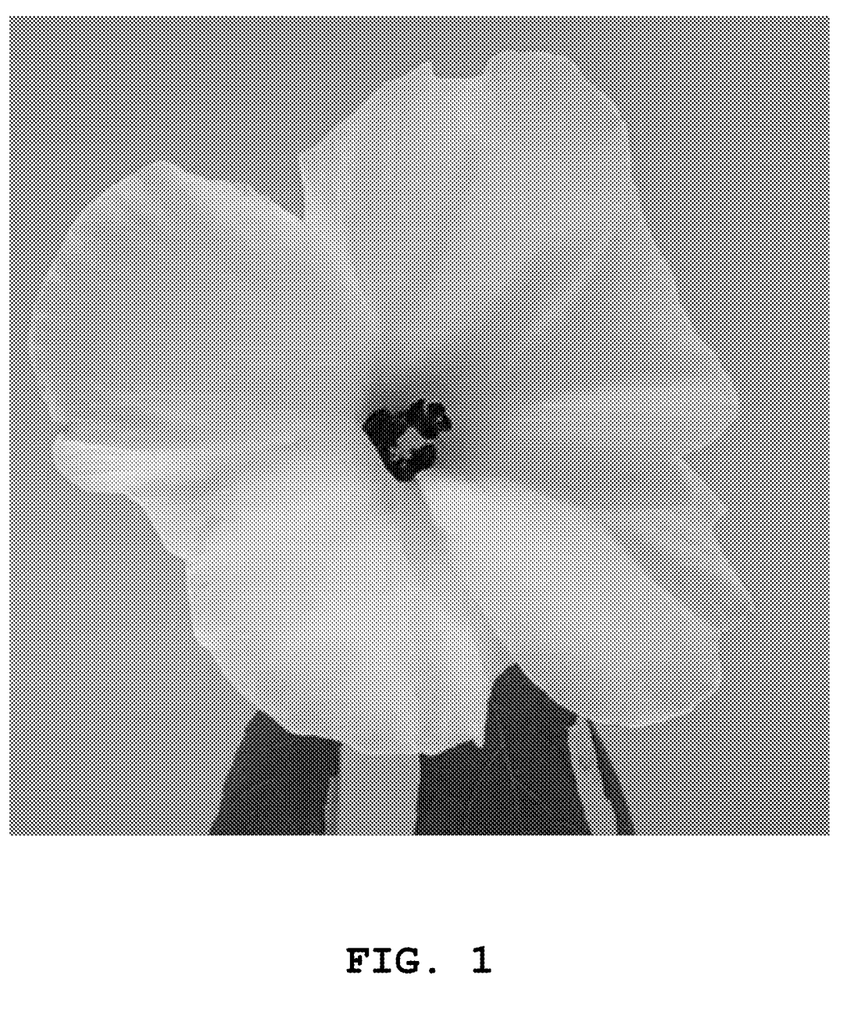
FIG. 1 is a picture showing *Hibiscus manihot* L. used in a cosmetic composition containing an extract of *Hibiscus manihot* L. of the present disclosure and a method for preparing the same.
Figure 2:
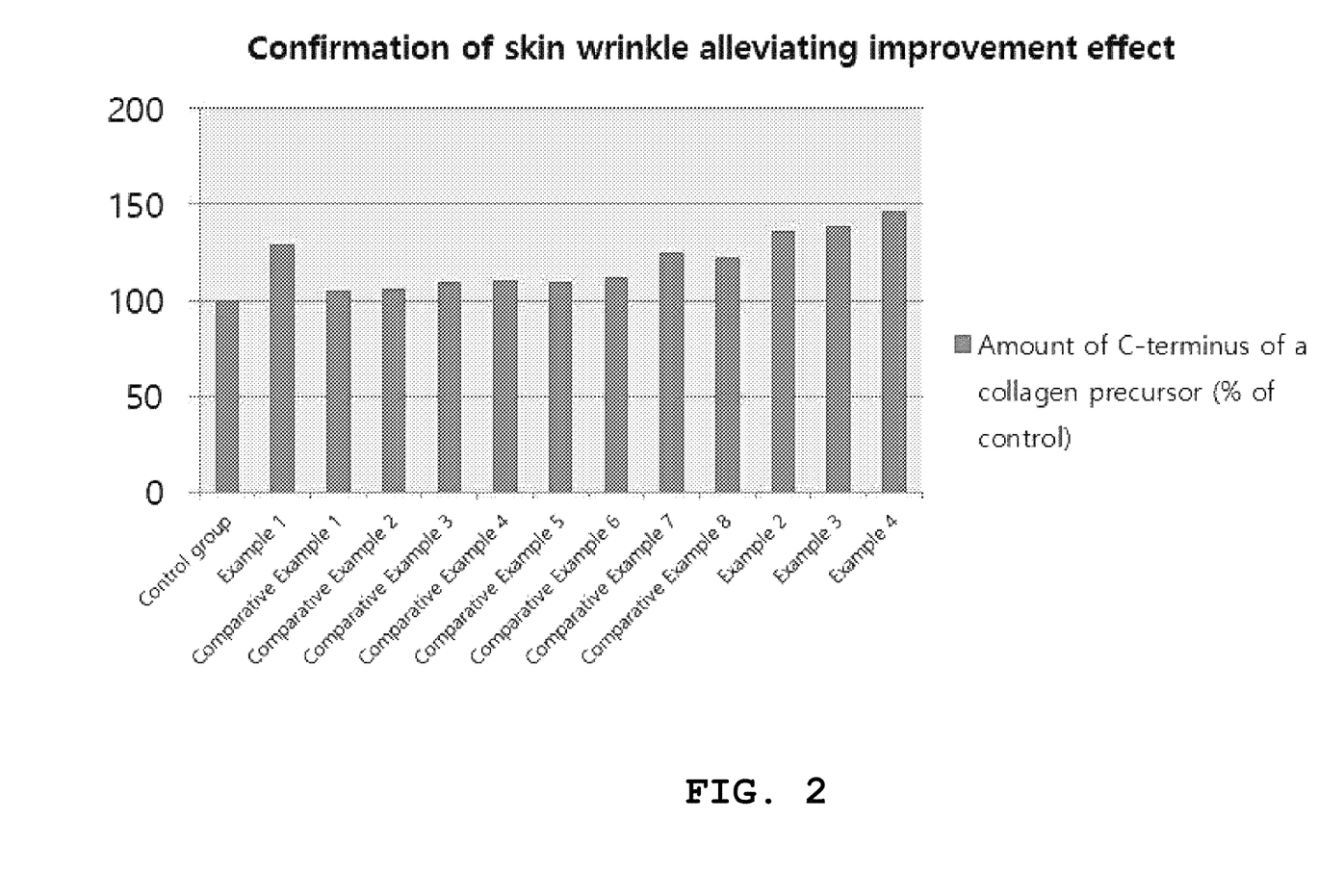
FIG. 2 is a graph showing an experiment for confirming a skin wrinkle alleviating effect with regard to Examples 1 to 4 and Comparative Examples 1 to 4 according to the present disclosure.
Figure 3:
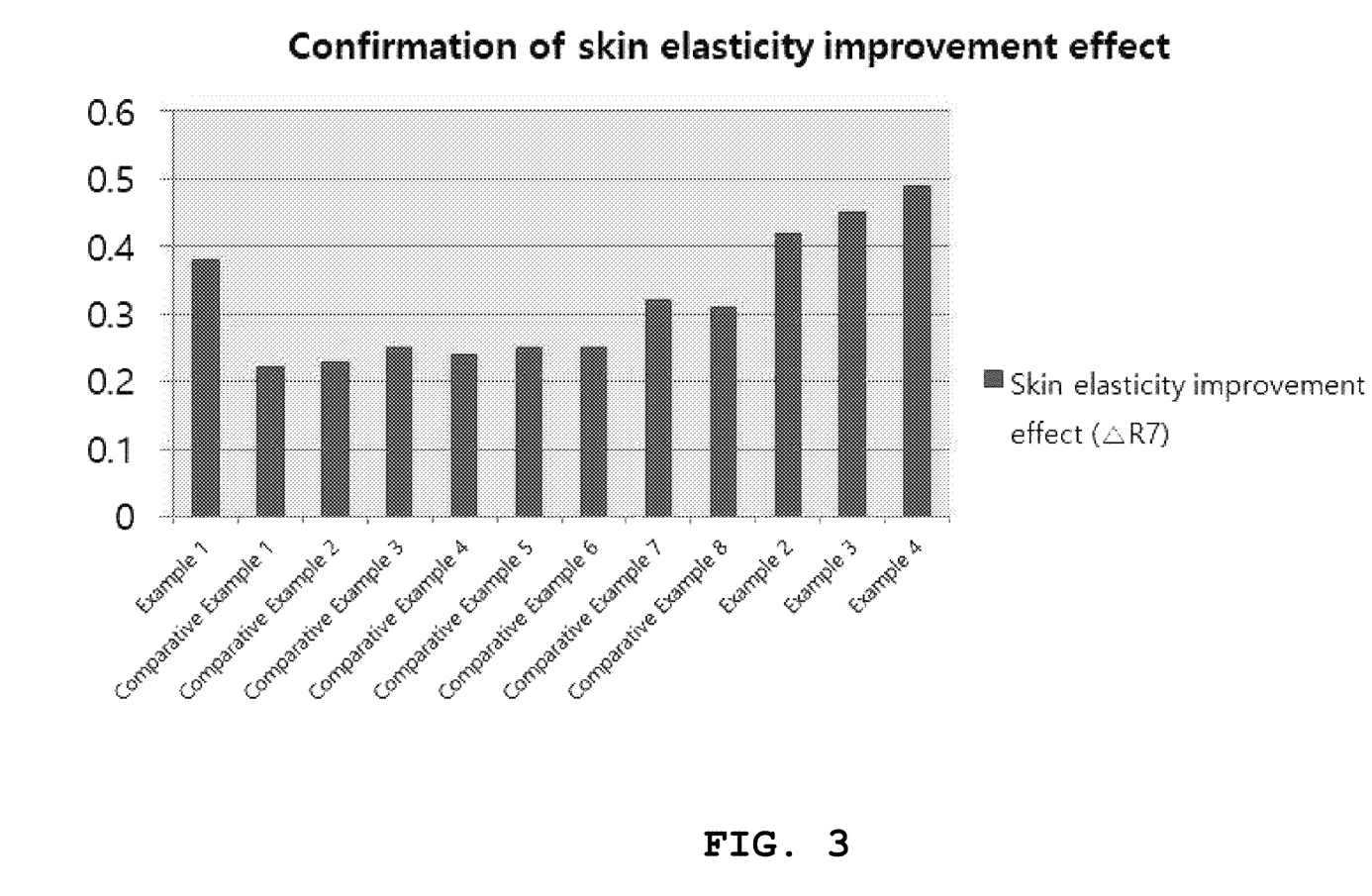
FIG. 3 is a graph showing an experiment for confirming a skin elasticity improving effect with regard to Examples 1 to 4 and Comparative Examples 1 to 4 according to the present disclosure.
Figure 4:
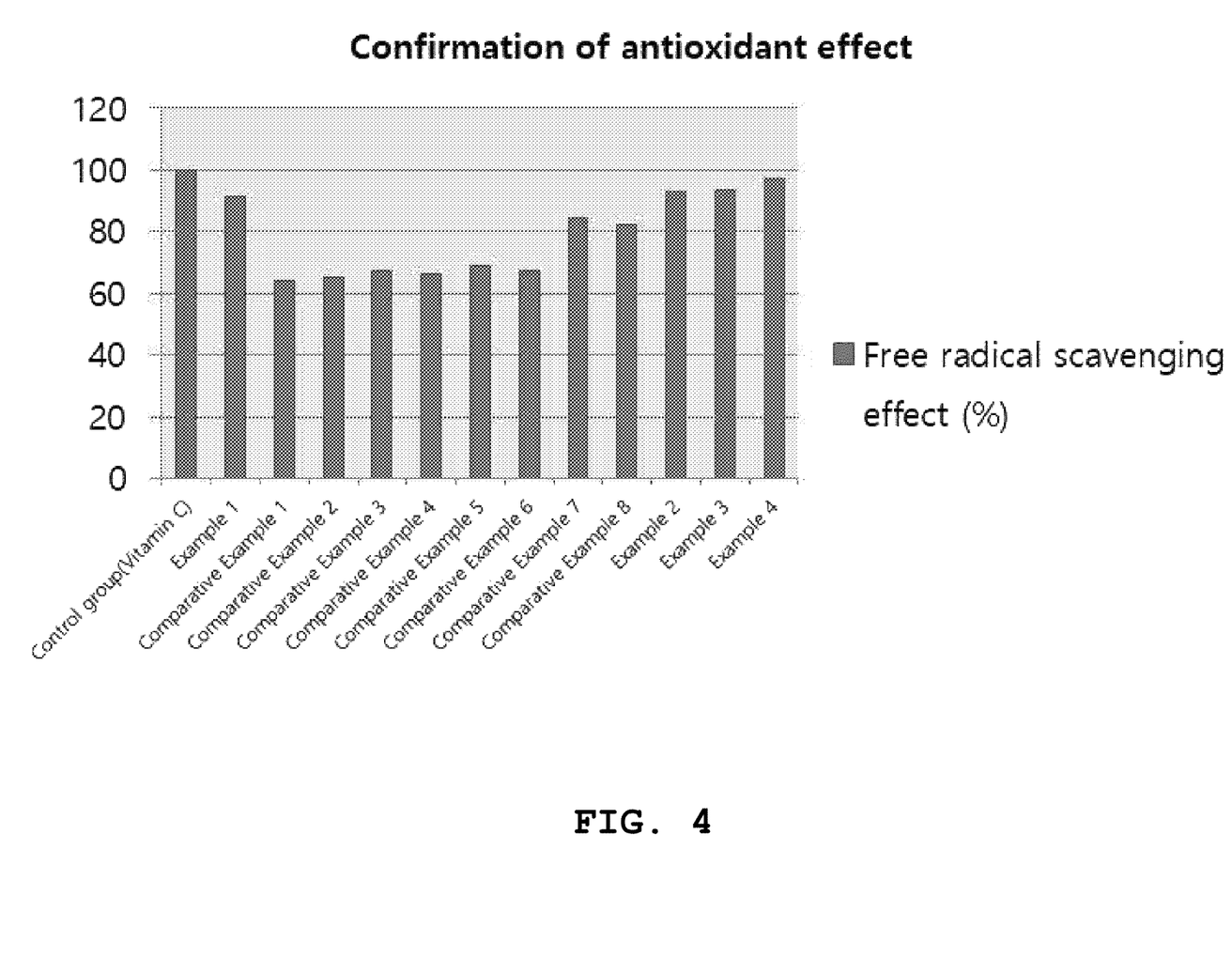
FIG. 4 is a graph showing an experiment for confirming an antioxidant effect with regard to Examples 1 to 4 and Comparative Examples 1 to 4 according to the present disclosure.
Figure 5:
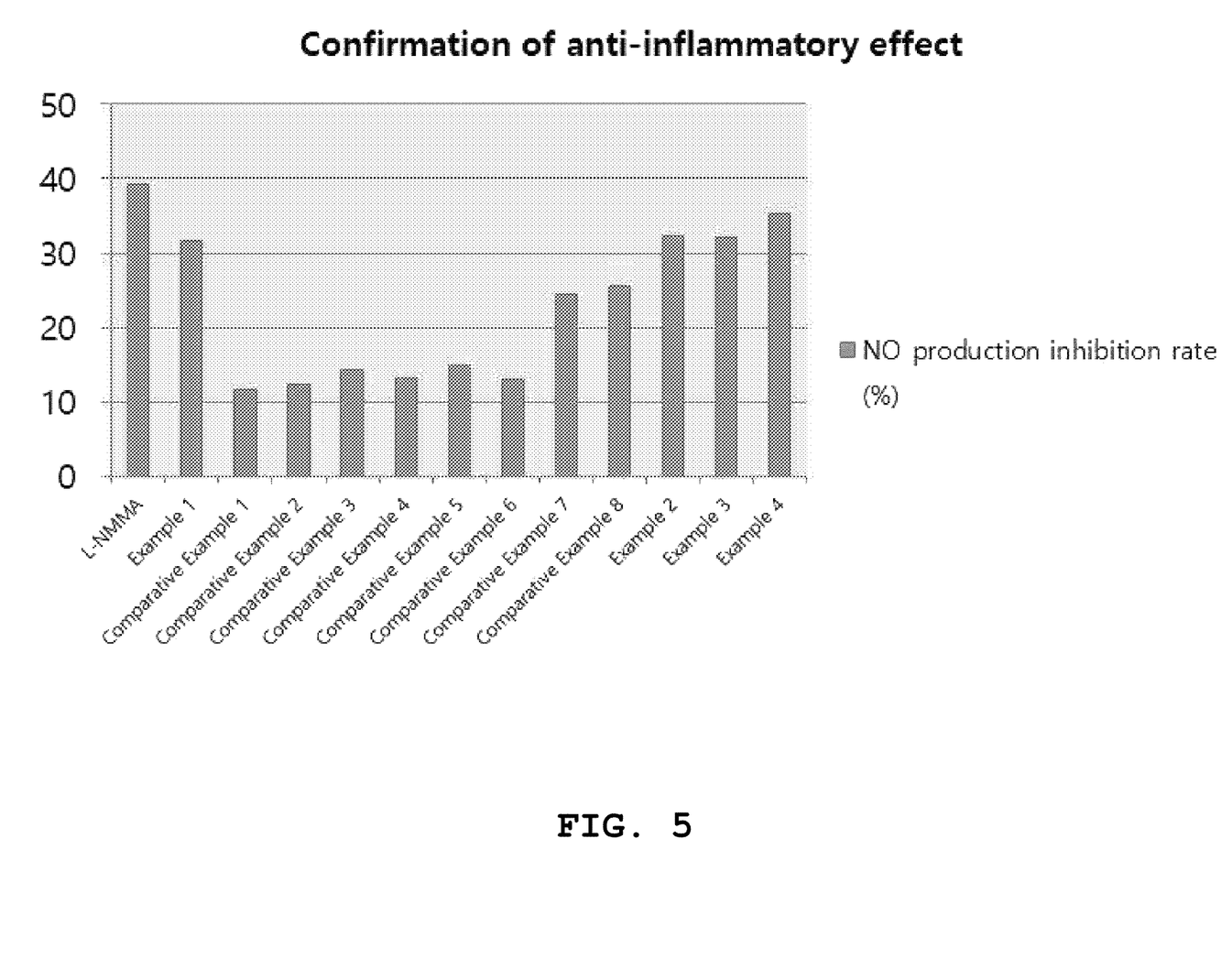
FIG. 5 is a graph showing an experiment for confirming an anti-inflammatory effect with regard to Examples 1 to 4 and Comparative Examples 1 to 4 according to the present disclosure.
Figure 6:
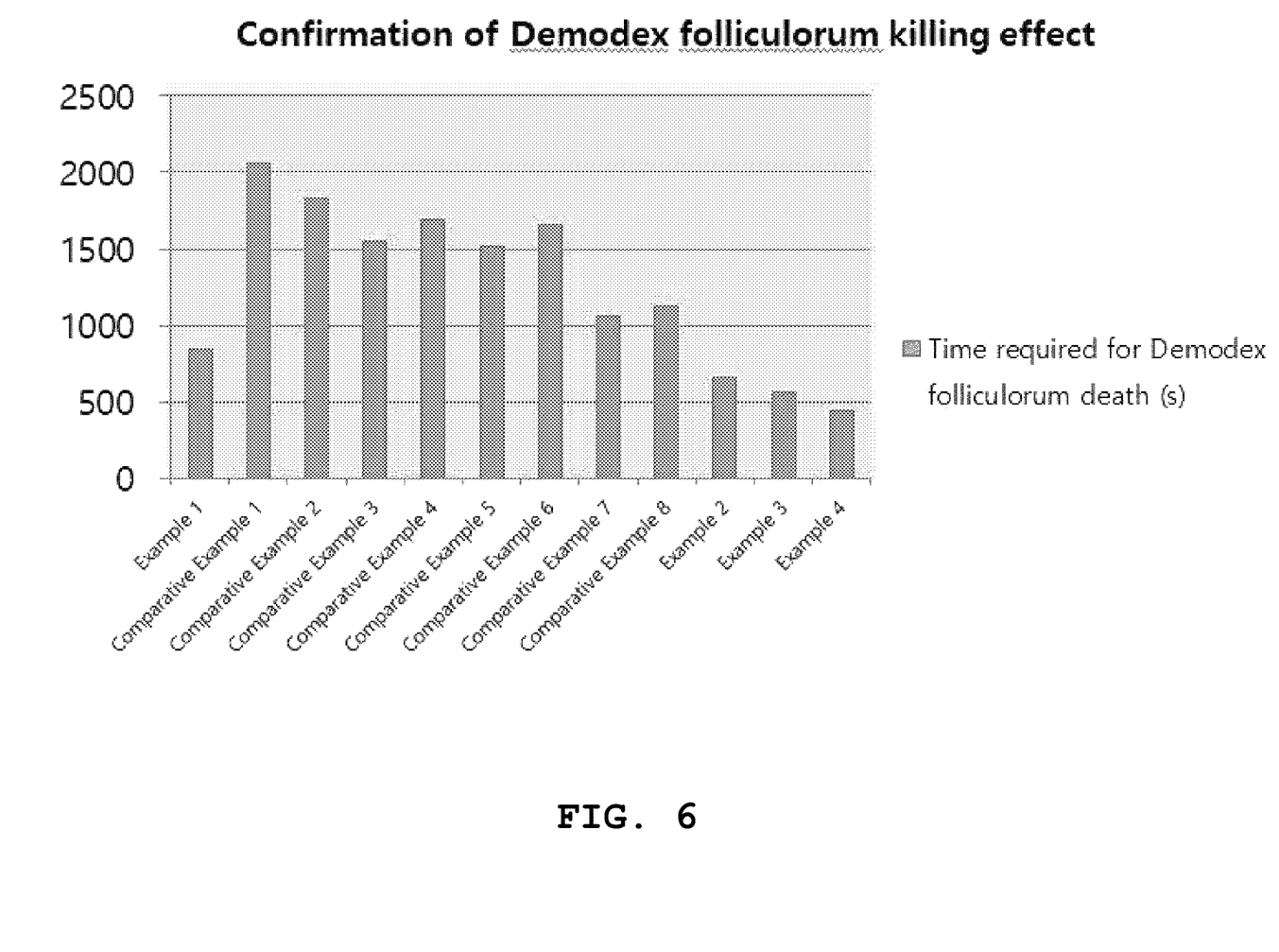
FIG. 6 is a graph showing an experiment for confirming a *Demodex folliculorum* killing effect with regard to Examples 1 to 4 and Comparative Examples 1 to 4 according to the present disclosure.
Figure 7:
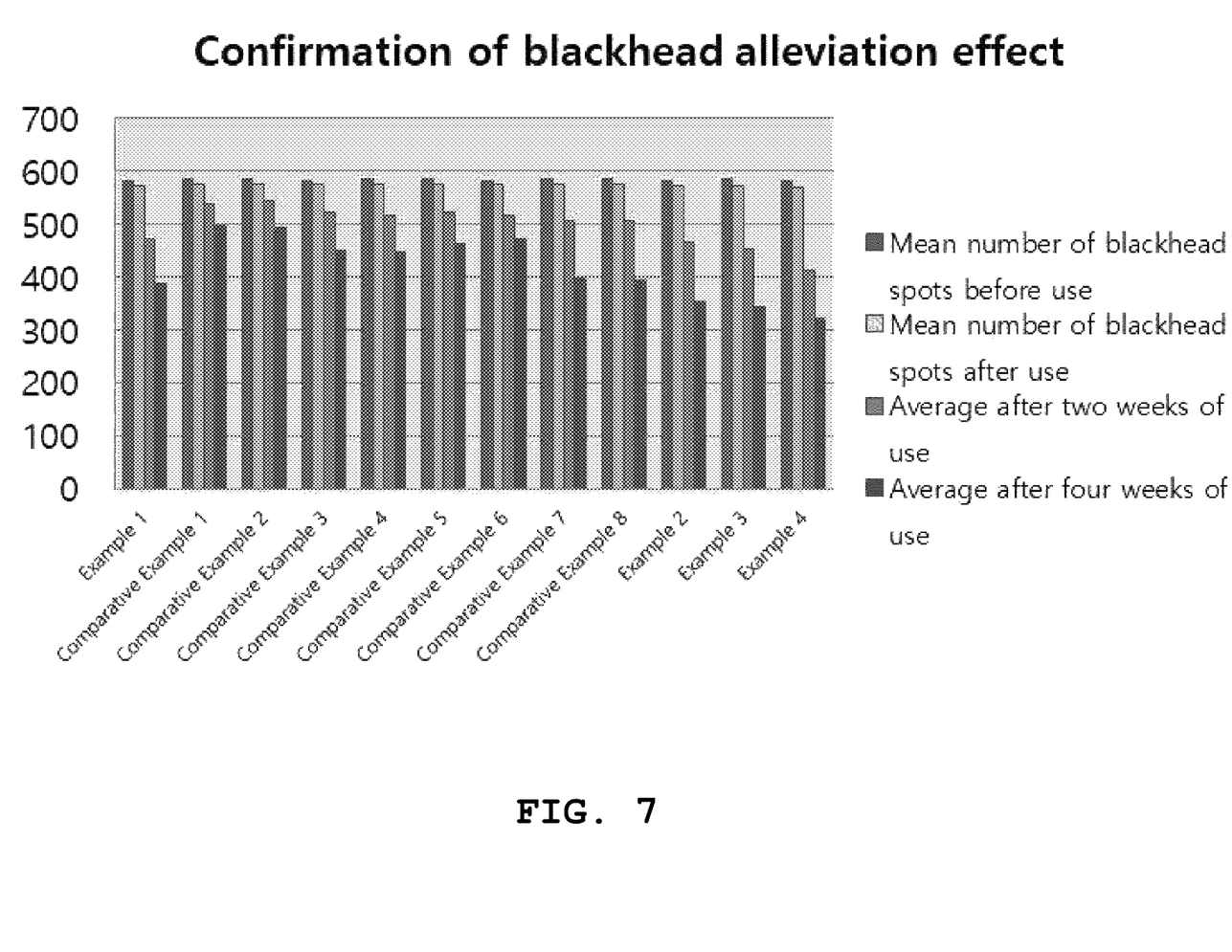
FIG. 7 is a graph showing an experiment for confirming a blackhead alleviating effect with regard to Examples 1 to 4 and Comparative Examples 1 to 4 according to the present disclosure.
Figure 8:
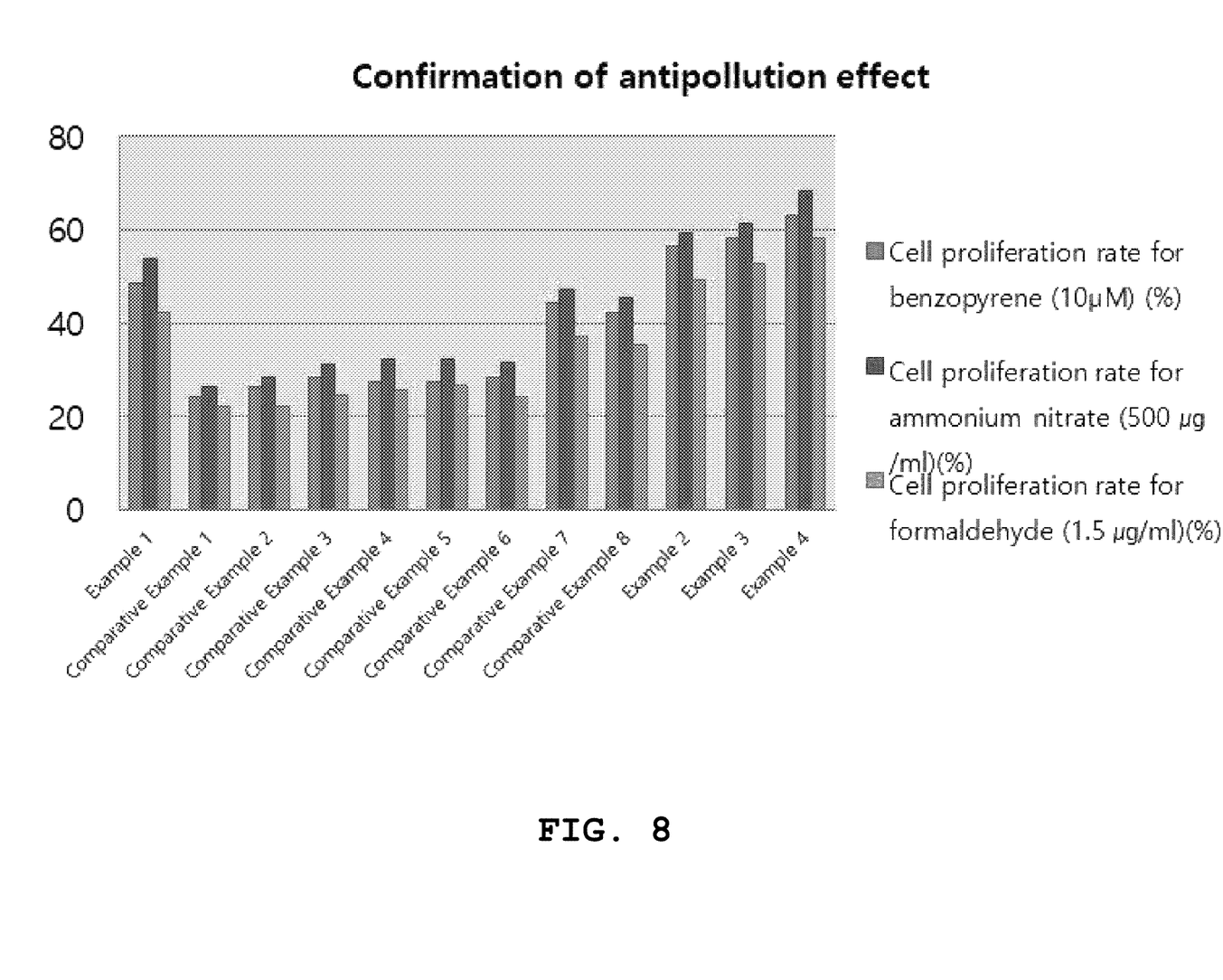
FIG. 8 is a graph showing an experiment for confirming an anti-pollution effect with regard to Examples 1 to 4 and Comparative Examples 1 to 4 according to the present disclosure.

The following detailed description of the present disclosure refers to embodiments in which the present disclosure may be practiced, and reference is made to the accompanying drawings shown by way of example of the corresponding embodiments. These embodiments are described in sufficient detail for those skilled in the art to practice the present disclosure. It is understood that various embodiments of the present disclosure are different from each other, but need not be mutually exclusive. For example, certain shapes, structures, and properties described herein may be implemented in other embodiments without departing from the spirit and scope of the present disclosure in relation to one embodiment. In addition, it is understood that the position or arrangement of individual components in each described embodiment may be changed without departing from the spirit and scope of the present disclosure.

Accordingly, the detailed description set forth below is not intended to be taken in a limiting sense, and the scope of the present disclosure, if properly described, is limited only by the appended claims, along with all scopes equivalent to those claimed by the claims. Like reference numerals in the drawings refer to the same or similar functions throughout the various aspects.

For the terms used in the present disclosure, general terms, which are currently widely used, have been selected with the consideration of the functions in the present disclosure, but may vary depending on a skilled person's intention or precedent in the art, the emergence of new technology, and the like. In addition, in a specific case, there is a term arbitrarily selected by the applicant, and in this case, the meaning will be described in detail in the corresponding description of the present disclosure. Thus, the term used in the present disclosure needs to be defined based on the meaning of the term and the overall content of the present disclosure, rather than the name of a simple term.

In the present disclosure, when a certain part is said to "include" a certain component, it is not meant to exclude other components, but meant to further include other components as well, unless otherwise especially specified.

Hereinafter, a cosmetic composition containing an extract of *Hibiscus manihot* L. according to the present disclosure will be described in detail.

The cosmetic composition containing the extract of *Hibiscus manihot* L. according to the present disclosure may have a feature of containing the extract of *Hibiscus manihot* L., which is obtained by performing a supercritical extraction on *Hibiscus manihot* L.

In the present disclosure, it may be preferable that the supercritical extraction is performed on a flower portion of *Hibiscus manihot* L.

In addition, the extract of *Hibiscus manihot* L. may be a supercritical extract of *Hibiscus manihot* L., which is obtained by performing the supercritical extraction on *Hibiscus manihot* L. through supercritical fluid containing carbon dioxide at a temperature of 40 to 120° C. and atmospheric pressure of 90 to 650.

Meanwhile, the extract of *Hibiscus manihot* L. may be obtained by performing the supercritical extraction on *Hibiscus manihot* L., through a continuous batch supercritical extraction method.

Accordingly, the extract of *Hibiscus manihot* L. may be obtained by performing the continuous batch supercritical extraction method of passing only carbon dioxide through *Hibiscus manihot* L. for 30 to 150 minutes, passing a fluid mixed with carbon dioxide and an auxiliary solvent for 30 to 150 minutes, and passing only carbon dioxide therethrough for the remaining 30 to 150 minutes.

The supercritical fluid may preferably contain carbon dioxide. Besides, the supercritical fluid may be a mixed fluid which is mixed with one or more co-solvents of purified water, ethanol, methanol, ethyl acetate, hexane or diethyl ether. In this case, the usable co-solvent may be preferably ethanol or an ethanol diluted in purified water.

At this time, the mixed fluid according to the present disclosure may be obtained by mixing carbon dioxide in an amount of 90% by volume with at least one co-solvent of ethanol, methanol, water, ethyl acetate, hexane, and diethyl ether in an amount of 10% by volume.

Meanwhile, the extract of *Hibiscus manihot* L. may be obtained by performing the supercritical extraction on *Hibiscus manihot* L., and capturing the same in nanoliposomes.

The capturing in nanoliposomes may be performed with a mixture containing the extract of *Hibiscus manihot* L., polyol, surfactant, phospholipid, fatty acid and water.

The extract of *Hibiscus manihot* L., may be preferably contained in an amount of 0.1 to 30.0% by weight based on the total weight of the nanoliposomes.

The polyol is not particularly limited, and the polyol used herein may be, for example, at least one selected from the group consisting of propylene glycol, dipropylene glycol, 1,3-butylene glycol, glycerin, methyl propanediol, isoprene glycol, pentylene glycol, erythritol, xylitol, sorbitol, and the like, and may be preferably propylene glycol. The polyol may be preferably contained in an amount of 0.1 to 70% by weight based on the total weight of the nanoliposomes.

The surfactant used herein may be anionic surfactants, cationic surfactants, amphoteric surfactants, and nonionic surfactants, and may be preferably anionic surfactants and nonionic surfactants. Specific examples of the anionic surfactant may include alkylacylglutamate, alkylphosphate, alkyllactylate, dialkylphosphate, trialkylphosphate, and the like. Specific examples of the nonionic surfactant may include alkoxylated alkyl ethers, alkoxylated alkyl esters, alkyl polyglycosides, polyglyceryl esters, sugar esters, and the like. Most preferably, polysorbates belonging to nonionic surfactants may be used. The amount of the surfactant used herein may be preferably 0.1 to 5.0% by weight based on the total weight of the nanoliposomes.

It may be good that the phospholipid used herein may be a natural phospholipid or a synthetic phospholipid, but may be preferably lecithin as a natural phospholipid. More preferably, the lecithin may be naturally-derived unsaturated lecithin or saturated lecithin extracted from soybean or egg yolk. The lecithin may be preferably contained in an amount of 0.1 to 8.0% by weight based on the total weight of the nanoliposomes.

The fatty acid may be a saturated or unsaturated fatty acid having a $C_{12-22}$ alkyl chain. For example, it may be appropriate to use any one or more of lauric acid, myristic acid, palmitic acid, stearic acid, oleic acid and linoleic acid. The fatty acid may be preferably contained in an amount of 0.1 to 3.0% by weight based on the total weight of the nanoliposomes.

It may be preferable to use purified water as the water, and the water may be preferably contained in the remaining amount when forming the nanoliposomes.

The preparation of the nanoliposomes may be performed through various methods, but may be most preferably prepared by applying a mixture containing the above ingredients and the supercritical extract of *Hibiscus manihot* L. to a high-pressure homogenizer. At this time, it may be preferable to prepare the nanoliposomes by passing the same through the high-pressure homogenizer two to four times under a pressure of 800 to 1000 bar.

The above-described method for preparing nanoliposomes is merely an example of a known method for preparing nanoliposomes, and the nanoliposomes may not be prepared only by the above-described preparation method.

In other words, the extract of *Hibiscus manihot* L. according to the present disclosure may be a supercritical extract of *Hibiscus manihot* L. or a supercritical extract of *Hibiscus manihot* L. which is captured in nanoliposomes.

The extract of *Hibiscus manihot* L. prepared as above may contain various ingredients to be included in cosmetic formulations, and may include, for example, stabilizers, solubilizers, vitamins, pigments, fragrances, chelating agents, or the like, and thus may be prepared in various formulations and thus may be commercially supplied.

Hereinafter, a method for preparing a cosmetic composition containing an extract of *Hibiscus manihot* L. according to the present disclosure will be described in detail.

The method for preparing a cosmetic composition containing an extract of *Hibiscus manihot* L. according to the present disclosure may include: a pulverizing step (S10) of pulverizing *Hibiscus manihot* L., to prepare pulverized *Hibiscus manihot* L.; and a supercritical extraction step (S20) of obtaining an extract of *Hibiscus manihot* L. by performing a supercritical extraction on *Hibiscus manihot* L. through supercritical fluid containing carbon dioxide.

First of all, the pulverizing step (S10) may be performed.

In the pulverizing step (S10), a process of pulverizing *Hibiscus manihot* L., to prepare pulverized *Hibiscus manihot* L. may be performed.

In the pulverizing step (S10), it may be appropriate to pulverize *Hibiscus manihot* L. to facilitate an elution of active ingredients from the *Hibiscus manihot* L.

In the pulverization step (S10), it may be appropriate to collect and pulverize the flower portions of *Hibiscus manihot* L.

Then, the supercritical extraction step (S20) may be performed.

In the supercritical extraction step (S20), a process of obtaining an extract by performing a supercritical extraction on the *Hibiscus manihot* L. pulverized in the pulverizing step (S10) through supercritical fluid containing carbon dioxide.

In this case, it may be appropriate to perform a supercritical extraction on the pulverized *Hibiscus manihot* L. through supercritical fluid containing carbon dioxide at a temperature of 40 to 120° C. and pressure of 90 to 650 in the supercritical extraction step (S20).

Meanwhile, the supercritical extraction step (S20) may include a first step of supercritical extraction with carbon dioxide alone (S21), a mixed fluid supercritical extraction step (S22), and a second step of supercritical extraction with carbon dioxide alone (S23). In other words, the supercritical extraction step (S20) may be performed through a continuous batch supercritical extraction method.

In the first step of supercritical extraction with carbon dioxide alone (S21), the supercritical extraction may be performed while only carbon dioxide flows through the pulverized *Hibiscus manihot* L. The first step of supercritical extraction with carbon dioxide alone (S21) may be performed for 30 to 150 minutes.

In the mixed fluid supercritical extraction step (S22), the supercritical extraction may be performed while a mixed fluid of carbon dioxide with co-solvent flows through the pulverized *Hibiscus manihot* L. The mixed fluid supercritical extraction step (S22) may be performed for 30 to 150 minutes. Meanwhile, the mixed fluid may be obtained by mixing carbon dioxide with at least one co-solvent of ethanol, methanol, water, ethyl acetate, hexane, and diethyl ether.

In the second step of supercritical extraction with carbon dioxide alone (S23), the supercritical extraction may be performed while only carbon dioxide flows again. The second step of supercritical extraction with carbon dioxide alone (S23) may be performed for 30 to 150 minutes.

It may be possible to obtain the skin elasticity improvement effect, the wrinkle alleviation effect, etc., of *Hibiscus manihot* L. through the continuous batch supercritical extraction process as described above.

Meanwhile, after performing the supercritical extraction step (S20), a nanoliposome capturing step (S30) of capturing the supercritical extract obtained in the supercritical extraction step (S20) into nanoliposomes may be further included.

In the nanoliposome capturing step (S30), it may be preferable to prepare a nanoliposome by mixing polyol, surfactant, phospholipid, fatty acid and water in the supercritical extract of *Hibiscus manihot* L., and applying the same to a high pressure homogenizer, and then passing through the high pressure homogenizer two to four times under a pressure of 800 to 1000 bar. The types of polyol, surfactant, phospholipid, and fatty acid may be appropriately selected and applied from the list described above in the previous paragraph.

Hereinafter, the effect of the cosmetic composition containing the extract of *Hibiscus manihot* L. according to the preparation method of the present disclosure will be described in detail through the following Examples, Comparative Examples, and Experimental Examples.

Example 1. Preparation of Composition Containing Supercritical Extract of *Hibiscus manihot* L A composition for testing according to Example 1 was prepared in accordance with the following preparation process.

Pulverization step (S10): the flower portions of *Hibiscus manihot* L. were pulverized to prepare *Hibiscus manihot* L.

Supercritical extraction step (S20): an extract was obtained by performing a supercritical extraction on the *Hibiscus manihot* L. pulverized in the pulverization step (S10) through carbon dioxide at a temperature of 80° C. and pressure of 350 for 270 minutes.

The obtained sample was mixed with purified water in a weight ratio of 1:10 to proceed with an experiment.

Comparative Example 1. Preparation of Composition Containing Hot Water Extract of *Hibiscus manihot* L A composition for testing according to Comparative Example 1 was prepared in accordance with the following preparation process.

Pulverization step (S10): the flower portions of *Hibiscus manihot* L. were pulverized to prepare *Hibiscus manihot* L.

Supercritical extraction step (S20): an extract was obtained by performing a hot water extraction on the *Hibiscus manihot* L. pulverized in the pulverization step (S10) through purified water at a temperature of 100° C. for 270 minutes.

The obtained sample was mixed with purified water in a weight ratio of 1:10 to proceed with an experiment.

Comparative Example 2. Preparation of Composition Containing Solvent Extract of *Hibiscus manihot* L A composition for testing according to Comparative Example 2 was prepared in accordance with the following preparation process.

Pulverization step (S10): the flower portions of *Hibiscus manihot* L. were pulverized to prepare *Hibiscus manihot* L.

Supercritical extraction step (S20): an extract was obtained by performing a solvent extraction on the *Hibiscus manihot* L. pulverized in the pulverization step (S10) through ethanol at a temperature of 100° C. for 270 minutes.

The obtained sample was mixed with purified water in a weight ratio of 1:10 to proceed with an experiment.

Comparative Example 3. Preparation of Composition Containing Hot Water Extract of *Hibiscus manihot* L. with Varying Extraction Conditions A composition for testing according to Comparative Example 3 was prepared in accordance with the following preparation process.

Pulverization step (S10): the flower portions of *Hibiscus manihot* L. were pulverized to prepare *Hibiscus manihot* L.

Supercritical extraction step (S20): an extract was obtained by performing a supercritical extraction on the *Hibiscus manihot* L. pulverized in the pulverization step (S10) through carbon dioxide at a temperature of 30° C. and atmospheric pressure of 350 for 270 minutes.

The obtained sample was mixed with purified water in a weight ratio of 1:10 to proceed with an experiment.

Comparative Example 4. Preparation of Composition Containing Hot Water Extract of *Hibiscus manihot* L. with Varying Extraction Conditions A composition for testing according to Comparative Example 4 was prepared in accordance with the following preparation process.

Pulverization step (S10): the flower portions of *Hibiscus manihot* L. were pulverized to prepare *Hibiscus manihot* L.

Supercritical extraction step (S20): an extract was obtained by performing a supercritical extraction on the *Hibiscus manihot* L. pulverized in the pulverization step (S10) through carbon dioxide at a temperature of 150° C. and atmospheric pressure of 350 for 270 minutes.

The obtained sample was mixed with purified water in a weight ratio of 1:10 to proceed with an experiment.

Comparative Example 5. Preparation of Composition Containing Hot Water Extract of *Hibiscus manihot* L. with Varying Extraction Conditions A composition for testing according to Comparative Example 5 was prepared in accordance with the following preparation process.

Pulverization step (S10): the flower portions of *Hibiscus manihot* L. were pulverized to prepare *Hibiscus manihot* L.

Supercritical extraction step (S20): an extract was obtained by performing a supercritical extraction on the *Hibiscus manihot* L. pulverized in the pulverization step (S10) through carbon dioxide at a temperature of 80° C. and atmospheric pressure of 80 for 270 minutes.

The obtained sample was mixed with purified water in a weight ratio of 1:10 to proceed with an experiment.

Comparative Example 6. Preparation of Composition Containing Hot Water Extract of *Hibiscus manihot* L. with Varying Extraction Conditions A composition for testing according to Comparative Example 6 was prepared in accordance with the following preparation process.

Pulverization step (S10): the flower portions of *Hibiscus manihot* L. were pulverized to prepare *Hibiscus manihot* L.

Supercritical extraction step (S20): an extract was obtained by performing a supercritical extraction on the *Hibiscus manihot* L. pulverized in the pulverization step (S10) through carbon dioxide at a temperature of 80° C. and atmospheric pressure of 700 for 270 minutes.

The obtained sample was mixed with purified water in a weight ratio of 1:10 to proceed with an experiment.

Comparative Example 7. Preparation of Composition Containing Supercritical Extract of Different Portions of *Hibiscus manihot* L A composition for testing according to Comparative Example 7 was prepared in accordance with the following preparation process.

Pulverization step (S10): the stem portions of *Hibiscus manihot* L. were pulverized to prepare *Hibiscus manihot* L.

Supercritical extraction step (S20): an extract was obtained by performing a supercritical extraction on the *Hibiscus manihot* L. pulverized in the pulverization step (S10) through carbon dioxide at a temperature of 80° C. and atmospheric pressure of 350 for 270 minutes.

The obtained sample was mixed with purified water in a weight ratio of 1:10 to proceed with an experiment.

Comparative Example 8. Preparation of Composition Containing Supercritical Extract of Different Portions of *Hibiscus manihot* L A composition for testing according to Comparative Example 8 was prepared in accordance with the following preparation process.

Pulverization step (S10): the root portions of *Hibiscus manihot* L. were pulverized to prepare *Hibiscus manihot* L.

Supercritical extraction step (S20): an extract was obtained by performing a supercritical extraction on the

*Hibiscus manihot* L. pulverized in the pulverization step (S10) through carbon dioxide at a temperature of 80° C. and atmospheric pressure of 350 for 270 minutes.

The obtained sample was mixed with purified water in a weight ratio of 1:10 to proceed with an experiment.

Example 2. Preparation of Composition Containing Supercritical Extract of *Hibiscus manihot* L. through Continuous Batch Critical Extraction A composition for testing according to Example 4 was prepared in accordance with the following preparation process.

Pulverization step (S10): the flower portions of *Hibiscus manihot* L. were pulverized to prepare *Hibiscus manihot* L.

First step of supercritical extraction with carbon dioxide alone (S21): the supercritical extraction was performed while only carbon dioxide flowed through the pulverized *Hibiscus manihot* L. for 90 minutes.

Mixed fluid supercritical extraction step (S22): the supercritical extraction was performed while a mixed fluid of carbon dioxide and ethanol in a volume ratio of 90:10 flowed through the pulverized *Hibiscus manihot* L.

Second step of supercritical extraction with carbon dioxide alone (S23): the supercritical extraction was performed while only carbon dioxide flowed again through the pulverized *Hibiscus manihot* L. for 90 minutes, so as to obtain a supercritical extract of *Hibiscus manihot* L.

The obtained sample was mixed with purified water in a weight ratio of 1:10 to proceed with an experiment.

Example 3. Preparation of Composition with Supercritical Extract of *Hibiscus manihot* L. Captured in Nanoliposome A composition for testing according to Example 4 was prepared in accordance with the following preparation process.

Pulverization step (S10): the flower portions of *Hibiscus manihot* L. were pulverized to prepare *Hibiscus manihot* L.

Supercritical extraction step (S20): an extract was obtained by performing a supercritical extraction on the *Hibiscus manihot* L. pulverized in the pulverization step (S10) through carbon dioxide at a temperature of 80° C. and atmospheric pressure of 350 for 270 minutes.

Nanoliposome capturing step (S30):

The obtained sample was mixed with purified water in a weight ratio of 1:10 to proceed with an experiment.

Example 4. Preparation of Composition Containing Supercritical Extract of *Hibiscus manihot* L. through Continuous Batch Critical Extraction Captured in Nanoliposome A composition for testing according to Example 4 was prepared in accordance with the following preparation process.

Pulverization step (S10): the flower portions of *Hibiscus manihot* L. were pulverized to prepare *Hibiscus manihot* L.

First step of supercritical extraction with carbon dioxide alone (S21): the supercritical extraction was performed while only carbon dioxide flowed through the pulverized *Hibiscus manihot* L. for 90 minutes.

Mixed fluid supercritical extraction step (S22): the supercritical extraction was performed while a mixed fluid of carbon dioxide and ethanol in a volume ratio of 90:10 flowed through the pulverized *Hibiscus manihot* L.

Second step of supercritical extraction with carbon dioxide alone (S23): the supercritical extraction was performed while only carbon dioxide flowed again through the pulverized *Hibiscus manihot* L. for 90 minutes, so as to obtain a supercritical extract of *Hibiscus manihot* L.

Nanoliposome capturing step (S30): 20% by weight of the supercritical extract of *Hibiscus manihot* L. obtained through the second step of supercritical extraction with carbon dioxide alone (S23), 30% by weight of propylene glycol as polyol, 2.0% by weight of polysorbate as a surfactant, 2.0% by weight of lecithin as phospholipid, 2.0% by weight of lauric acid as fatty acid, and purified water in the remaining amount were mixed and applied to a high atmospheric pressure homogenizer, so as to prepare nanoliposome.

The obtained sample was mixed with purified water in a weight ratio of 1:10 to proceed with an experiment.

Experimental Example 1. Confirmation of Skin Wrinkle Alleviation Effect

A wrinkle alleviation effect was confirmed with respect to Examples 1 to 4 and Comparative Examples 1 to 8.

Skin fibroblasts (HDFn) were inoculated in a 48-well plate with 0.3 mL of culture medium at a concentration of $5 \times 10^4$ cells/well and cultured at 37° C. and 5% $CO_2$. In 24 hours later, the cells were cultured for 24 hours with a fresh medium containing Examples 1 to 4 and Comparative Examples 1 to 8. After culturing for 24 hours, the culture medium was collected and an amount of C-terminus of a collagen precursor was measured by using an enzymes-linked immunoassay kit (Takara Corporation). In addition, an amount of collagen in the medium was calculated by obtaining a standard curve between 0 ng and 640 ng of collagen using a collagen solution of 640 ng/mL.

TABLE 1

|  | Amount of C-terminus of a collagen precursor (% of control) |
|---|---|
| Control group | 100.00 |
| Example 1 | 128.65 |
| Comparative Example 1 | 104.87 |
| Comparative Example 2 | 105.46 |
| Comparative Example 3 | 109.25 |
| Comparative Example 4 | 110.34 |
| Comparative Example 5 | 108.78 |
| Comparative Example 6 | 111.49 |
| Comparative Example 7 | 124.31 |
| Comparative Example 8 | 122.22 |
| Example 2 | 136.18 |
| Example 3 | 138.43 |
| Example 4 | 145.95 |

As a result, it was confirmed that the composition of Example 1 has a superior effect compared to Comparative Examples 1 to 8. Meanwhile, Examples 2 to 4, which were subjected to an additional procedure, showed a somewhat higher effect than that of Example 1. Accordingly, it was confirmed that an unexpected effect occurs according to the preparation method of the present disclosure.

Experimental Example 2. Confirmation of Skin Elasticity Improvement Effect

The skin elasticity improvement effect was evaluated by performing an experiment on a skin elasticity improvement effect on the samples prepared in Examples 1 to 4 and Comparative Examples 1 to 8 with regard to humans.

The cosmetics used in the experiment were samples prepared in Examples 1 to 4 and Comparative Examples 1 to 8. The samples prepared in Examples 1 to 4 and Comparative Examples 1 to 8 were applied to each portion of the face twice a day for two consecutive months with respect to 20 experimenters (females aged 20-35 years).

After completion of the experiment, the skin elasticity improvement effect was measured by using a skin elasticity meter (cutometer SEM 575, C+K Electronic Co., Germany) before and after using the product for two months.

Experimental results are described as ΔR7 values of Cutometer SEM 575 in table 2 below and R7 values indicate viscoelasticity of the skin. As shown in table 2, it may be seen that the skin elasticity improvement effect is excellent when Examples 1 to 4 are applied.

TABLE 2

| | Skin elasticity improvement effect (ΔR7) |
|---|---|
| Example 1 | 0.38 |
| Comparative Example 1 | 0.22 |
| Comparative Example 2 | 0.23 |
| Comparative Example 3 | 0.25 |
| Comparative Example 4 | 0.24 |
| Comparative Example 5 | 0.25 |
| Comparative Example 6 | 0.25 |
| Comparative Example 7 | 0.32 |
| Comparative Example 8 | 0.31 |
| Example 2 | 0.42 |
| Example 3 | 0.45 |
| Example 4 | 0.49 |

As a result, it was confirmed that the composition of Example 1 has a superior effect compared to Comparative Examples 1 to 8. Meanwhile, Examples 2 to 4, which were subjected to an additional procedure, showed a somewhat higher effect than that of Example 1. Accordingly, it was confirmed that an unexpected effect occurs according to the preparation method of the present disclosure.

Experimental Example 3. Confirmation of Antioxidant Effect

An antioxidant effect experiment was performed to confirm an antioxidant effect of Examples 1 to 4 and Comparative Examples 1 to 8 through a free radical scavenging effect using a DPPH method according to a known method.

100 μl of Examples 1 to 4 and Comparative Examples 1 to 8 were dispensed into 96 microplates, and 10 μl of a 2,2-diphenyl-1-picrylhydrazyl (DPPH) solution dissolved in ethanol to reach 1 mM was added thereto. After a reaction in 30 minutes later at room temperature, absorbance was measured at 517 nm to measure a free radical scavenging activity. An experiment was performed with vitamin C at a concentration of 0.1% as a control group along with the compositions of Examples 1 to 4 and Comparative Examples 1 to 8. The results are shown in table 3 based on the free radical scavenging effect of vitamin C as 100%.

TABLE 3

| | Free radical scavenging effect (%) |
|---|---|
| Control (vitamin C) | 100 |
| Example 1 | 91.5 |
| Comparative Example 1 | 64.2 |
| Comparative Example 2 | 65.1 |
| Comparative Example 3 | 67.3 |
| Comparative Example 4 | 66.4 |

TABLE 3-continued

| | Free radical scavenging effect (%) |
|---|---|
| Comparative Example 5 | 68.7 |
| Comparative Example 6 | 67.5 |
| Comparative Example 7 | 84.4 |
| Comparative Example 8 | 82.3 |
| Example 2 | 92.9 |
| Example 3 | 93.3 |
| Example 4 | 97.2 |

As a result, it was confirmed that the composition of Example 1 has a superior effect compared to Comparative Examples 1 to 8. Meanwhile, Examples 2 to 4, which were subjected to an additional procedure, showed a somewhat higher effect than that of Example 1. Accordingly, it was confirmed that an unexpected effect occurs according to the preparation method of the present disclosure.

Experimental Example 4. Confirmation of Anti-Inflammatory Effect

An anti-inflammatory effect was confirmed with respect to above Examples 1 to 4 and Comparative Examples 1 to 8.

In order to confirm the anti-inflammatory effect and skin trouble alleviation effect of Examples 1 to 4 and Comparative Examples 1 to 8, an experiment on nitric oxide (NO) formation inhibitory power was performed with a GRIESS method using RAW264.7 cell lines (ATCC number: CRL-2278).

Specifically, RAW264.7 cells, which are mouse macrophages, were subcultured several times and placed in a 24-well plate so that $3 \times 10^5$ cells were put into each well, and then incubated for 24 hours. Then, Examples 1 to 4 and Comparative Examples 1 to 8 were replaced with a diluted cell medium at a concentration of 10 ppm. At this time, L-NMMA (L-NG-Monomethylarginine), a NO-production inhibitor, was treated together as a positive control and incubated for 30 minutes, and then 1 μg of lipopolysaccharide (LPS) was treated as a stimulus and cultured for 24 hours. 100 μl of the supernatant was transferred to a 96-well plate and reacted at room temperature for 10 minutes with the addition of 100 μl of GRIESS solution, so as to measure the absorbance at 540 nm, thereby determining an NO inhibitory effect of the compound of Formula 1, and the results are shown in table 4 below.

TABLE 4

| Sample | NO production inhibition rate (%) |
|---|---|
| Control (DMSO, 10 ppm) | — |
| L-NMMA (positive control, 10 ppm) | 39.14 |
| Example 1 | 31.56 |
| Comparative Example 1 | 11.67 |
| Comparative Example 2 | 12.36 |
| Comparative Example 3 | 14.24 |
| Comparative Example 4 | 13.27 |
| Comparative Example 5 | 14.88 |
| Comparative Example 6 | 13.07 |
| Comparative Example 7 | 24.47 |
| Comparative Example 8 | 25.68 |
| Example 2 | 32.22 |
| Example 3 | 32.11 |
| Example 4 | 35.33 |

As a result, it was confirmed that the composition of Example 1 has a superior effect compared to Comparative Examples 1 to 8. Meanwhile, Examples 2 to 4, which were subjected to an additional procedure, showed a somewhat higher effect than that of Example 1. Accordingly, it was confirmed that an unexpected effect occurs according to the preparation method of the present disclosure.

Experimental Example 5. Confirmation of *Demodex Folliculorum* Killing Effect

A *Demodex folliculorum* survival inhibitory effect was confirmed through the following method with respect to Examples 1 to 4 and Comparative Examples 1 to 8.

First of all, an electron microscope was attached to a CCD camera and then connected to a computer. *Demodex folliculorum* was collected from hair follicles using a blade and placed on a slide glass, after which Examples 1 to 4 and Comparative Examples 1 to 8 were dropped thereon, and the movement of the body and legs of the *Demodex folliculorum* was observed. At this time, an appearance of *Demodex folliculorum* was observed with an electron microscope at a low magnification and a detailed appearance was observed at an increasingly high magnification while checking a time and measuring a survival time. In the experiment, the survival time refers to a time required from the time when the sample was dropped to the time when the *Demodex folliculorum* body shrank and stopped moving and death was confirmed. The experimental group in which physiological saline was dropped on *Demodex folliculorum* was used as a control group.

TABLE 5

| | Time required for Demodex folliculorum death (s) |
|---|---|
| Control group | Not dead |
| Example 1 | 845 sec |
| Comparative Example 1 | 2056 sec |
| Comparative Example 2 | 1828 sec |
| Comparative Example 3 | 1545 sec |
| Comparative Example 4 | 1692 sec |
| Comparative Example 5 | 1516 sec |
| Comparative Example 6 | 1654 sec |
| Comparative Example 7 | 1064 sec |
| Comparative Example 8 | 1132 sec |
| Example 2 | 664 sec |
| Example 3 | 568 sec |
| Example 4 | 442 sec |

As a result, it was confirmed that the composition of Example 1 has a superior effect compared to Comparative Examples 1 to 8. Meanwhile, Examples 2 to 4, which were subjected to an additional procedure, showed a somewhat higher effect than that of Example 1. Accordingly, it was confirmed that an unexpected effect occurs according to the preparation method of the present disclosure.

Experimental Example 6. Confirmation of Blackhead Removing Effect

A blackhead removing effect was tested by using Examples 1 to 4 and Comparative Examples 1 to 8.

An analysis of blackhead spots was performed by using Facial stage DM3 (Moritex, Japan) which quantifies the same. After dividing 60 testers into five groups, Examples 1 to 2 and Comparative Examples 1 to 3 were applied to the nose for four weeks. The number of red spots in the FL pictures was compared in the nose area (width 180, height 100 pixel), which is a measurement site before and after use of the product, and the results are shown in table 6 below.

TABLE 6

| | Mean number of blackhead spots before use | Mean number of blackhead spots after use | Average after two weeks of use Number of blackhead spots | Average after four weeks of use Number of blackhead spots |
|---|---|---|---|---|
| Example 1 | 582.7 | 574.5 | 472.1 | 388.9 |
| Comparative Example 1 | 584.5 | 577.3 | 537.2 | 497.3 |
| Comparative Example 2 | 585.4 | 577.2 | 546.3 | 495.2 |
| Comparative Example 3 | 583.5 | 576.7 | 524.4 | 451.5 |
| Comparative Example 4 | 586.1 | 576.4 | 516.6 | 448.2 |
| Comparative Example 5 | 585.2 | 576.1 | 524.3 | 463.3 |
| Comparative Example 6 | 582.8 | 576.2 | 515.7 | 473.4 |
| Comparative Example 7 | 585.5 | 575.3 | 506.8 | 397.2 |
| Comparative Example 8 | 584.3 | 575.7 | 507.2 | 395.1 |
| Example 2 | 582.4 | 573.7 | 465.2 | 355.2 |
| Example 3 | 586.5 | 572.6 | 454.3 | 344.3 |
| Example 4 | 583.7 | 571.4 | 412.8 | 323.5 |

As a result, it was confirmed that the composition of Example 1 has a superior effect compared to Comparative Examples 1 to 8. Meanwhile, Examples 2 to 4, which were subjected to an additional procedure, showed a somewhat higher effect than that of Example 1. Accordingly, it was confirmed that an unexpected effect occurs according to the preparation method of the present disclosure.

Experimental Example 7. Confirmation of Antipollution Effect

An antipollution effect was confirmed with respect to Examples 1 to 4 and Comparative Examples 1 to 8.

The anti-pollution effect was generally confirmed by a known method using skin keratinocytes which come into direct contact with pollutants. When Examples 1 to 4 and Comparative Examples 1 to 8 were mixed together using benzopyrene, ammonium nitrate, and formaldehyde, which are main contaminants in the air, the effect of inhibiting skin cell damage caused by contaminants was confirmed by measuring the degree of survival of skin keratinocytes.

Human keratinocytes HaCaT were dispensed in a 96-well plate at a concentration of $5 \times 10^3$ cells/ml and cultured for 24 hours, were treated with benzopyrene (10 µM), ammonium nitrate (500 µg/ml), formaldehyde (1.5 µg/ml), Examples 1 to 4 and Comparative Examples 1 to 8 respectively, and further cultured for 48 hours. After that, MTT solution was added at a concentration of 5 mg/ml and incubated for three hours, after which the medium was removed, and then 150 ul of dimethyl sulfoxide was added to each well and shaken for 10 minutes, so as to measure the absorbance at 570 nm.

TABLE 7

| | Contaminants | | |
|---|---|---|---|
| | Cell proliferation rate for benzopyrene (10 μM) (%) | Cell proliferation rate for ammonium nitrate (500 μg/ml) (%) | Cell proliferation rate for formaldehyde (1.5 μg/ml) (%) |
| Example 1 | 48.5 | 53.8 | 42.2 |
| Comparative Example 1 | 24.4 | 26.5 | 22.1 |
| Comparative Example 2 | 26.2 | 28.3 | 22.3 |
| Comparative Example 3 | 28.4 | 31.2 | 24.5 |
| Comparative Example 4 | 27.5 | 32.3 | 25.7 |
| Comparative Example 5 | 27.4 | 32.3 | 26.8 |
| Comparative Example 6 | 28.3 | 31.5 | 24.4 |
| Comparative Example 7 | 44.3 | 47.2 | 37.2 |
| Comparative Example 8 | 42.2 | 45.5 | 35.3 |
| Example 2 | 56.7 | 59.2 | 49.4 |
| Example 3 | 58.3 | 61.3 | 52.6 |
| Example 4 | 63.2 | 68.4 | 58.2 |

As a result, it was confirmed that the composition of Example 1 has a superior effect compared to Comparative Examples 1 to 8. Meanwhile, Examples 2 to 4, which were subjected to an additional procedure, showed a somewhat higher effect than that of Example 1. Accordingly, it was confirmed that an unexpected effect occurs according to the preparation method of the present disclosure.

CONCLUSION

Through above Examples 1 to 4, Comparative Examples 1 to 8, and Experimental Examples 1 to 7, the effect of the cosmetic composition containing the extract of *Hibiscus manihot* L. according to the preparation method of the present disclosure was confirmed.

The skin wrinkle alleviation effect was confirmed through Experimental Example 1, the skin elasticity improvement effect was confirmed through Experimental Example 2, the antioxidant effect was confirmed through Experimental Example 3, the anti-inflammatory effect was confirmed through Experimental Example 4, the *Demodex folliculorum* killing effect was confirmed through Experimental Example 5, the blackhead removing effect was confirmed through Experimental Example 6, and the anti-pollution effect was confirmed through Experimental Example 7.

In addition, in the case of varying the extraction method, the temperature or pressure conditions of extraction, and the extraction site, it was confirmed that Comparative Examples 1 to 8 show a significantly lower than that of Example 1, and it was confirmed that unexpected effects are obtained according to the preparation method of the present disclosure.

Meanwhile, in the case of Examples 2 to 4 in which the method of supercritical extraction is specifically limited or a supercritical extract is nanoliposome, it was confirmed that there is a somewhat higher effect than that of Example 1. Thus, with respect to the preparation method described in the present disclosure, it is shown that the extract of *Hibiscus manihot* L. has an unexpected effect on the anti-wrinkle alleviation effect and the skin elasticity improvement effect as well as the antioxidant effect, the anti-inflammatory effect, the *Demodex folliculorum* killing effect, the blackhead removing effect, and the anti-pollution effect.

Accordingly, through one aspect of the present disclosure, provided are a cosmetic composition containing an extract of *Hibiscus Manihot* L. and a method for preparing the same, which contains the extract of *Hibiscus Manihot* L., thus having the effect of improving skin elasticity, alleviating skin wrinkles, etc.

Although the present disclosure has been described with the accompanying drawings, this is only one embodiment of various embodiments including the gist of the present disclosure, and is intended to be easily implemented by those of ordinary skill in the art. For the purpose, it is clear that the present disclosure is not limited to the embodiments described above. Thus, the protection scope of the present disclosure needs to be construed by the following claims, and all technical ideas within the equivalent range by changes, substitutions, substitutions, etc. within the scope not departing from the gist of the present disclosure will be included in the rights of the present disclosure. In addition, it is clear that some components of the drawings are provided to be exaggerated or reduced than the actual ones for more clearly explaining the configuration.

What is claimed is:

1. A cosmetic composition comprising an extract of *Hibiscus manihot* L., wherein the cosmetic composition comprises an extract of *Hibiscus manihot* L. obtained by performing a continuous batch supercritical extraction on a flower portion of *Hibiscus manihot* L,
wherein performing the continuous batch supercritical extraction comprises the steps of:
   flowing only carbon dioxide through the flower portion of *Hibiscus manihot* L for 30 to 150 minutes,
   flowing a mixed fluid of about 90% by volume carbon dioxide and about 10% by volume of at least one co-solvent selected from ethanol, methanol, water, ethyl acetate, hexane, and diethyl ether through the flower portion of *Hibiscus manihot* L for 30 to 150 minutes, and
   flowing only carbon dioxide through the flower portion of *Hibiscus manihot* L for another 30 to 150 minutes.

2. The cosmetic composition of claim 1, wherein the extract of *Hibiscus manihot* L. is obtained by performing the continuous batch supercritical extraction on the flower portion of *Hibiscus manihot* L. through supercritical fluid comprising carbon dioxide at a temperature of 40 to 120° C. and atmospheric pressure of 90 to 650.

* * * * *